United States Patent
Munoz

[11] Patent Number: 6,146,402
[45] Date of Patent: Nov. 14, 2000

[54] ENDOTRACHEAL TUBE GUIDE INTRODUCER AND METHOD OF INTUBATION

[76] Inventor: Cayetano S. Munoz, 35 W. Condrad Dr., Phoenix, Ariz. 85023

[21] Appl. No.: 09/239,221

[22] Filed: Jan. 28, 1999

Related U.S. Application Data

[63] Continuation-in-part of application No. 08/871,369, Jun. 9, 1997, abandoned.

[51] Int. Cl.⁷ .................................................. A61M 29/00
[52] U.S. Cl. ............................................................. 606/194
[58] Field of Search ..................................... 606/194, 206, 606/108; 600/199, 194, 114, 120

[56] References Cited

U.S. PATENT DOCUMENTS

| | | | |
|---|---|---|---|
| 5,285,778 | 2/1994 | Mackin | 600/194 |
| 5,329,940 | 7/1994 | Adair | 600/120 |
| 5,607,386 | 3/1997 | Flam | 600/120 |
| 5,645,519 | 7/1997 | Lee et al. | 600/194 |
| 5,665,052 | 9/1997 | Bullard | 600/194 |
| 5,842,973 | 12/1998 | Bullard | 600/194 |

Primary Examiner—Michael Buiz
Assistant Examiner—(Jackie) Tan-Uyen T. Ho
Attorney, Agent, or Firm—Gregory J. Nelson

[57] ABSTRACT

An Endotracheal tube guide introducer having a rigid tube with a lumen. A handle is attached to one end and the distal end of the tube is curved. The tube includes visualization means such as a fiberoptic tube. An aperture in the handle intercepts the lumen to facilitate insertion of a flexible guide tube. A port for attachment of a light may be provided on the handle. A guide line is inserted into the larynx by use of the introducer. The introducer is removed and an endotracheal tube (ET) may then be advanced into the trachea along the guide line until properly positioned.

11 Claims, 4 Drawing Sheets

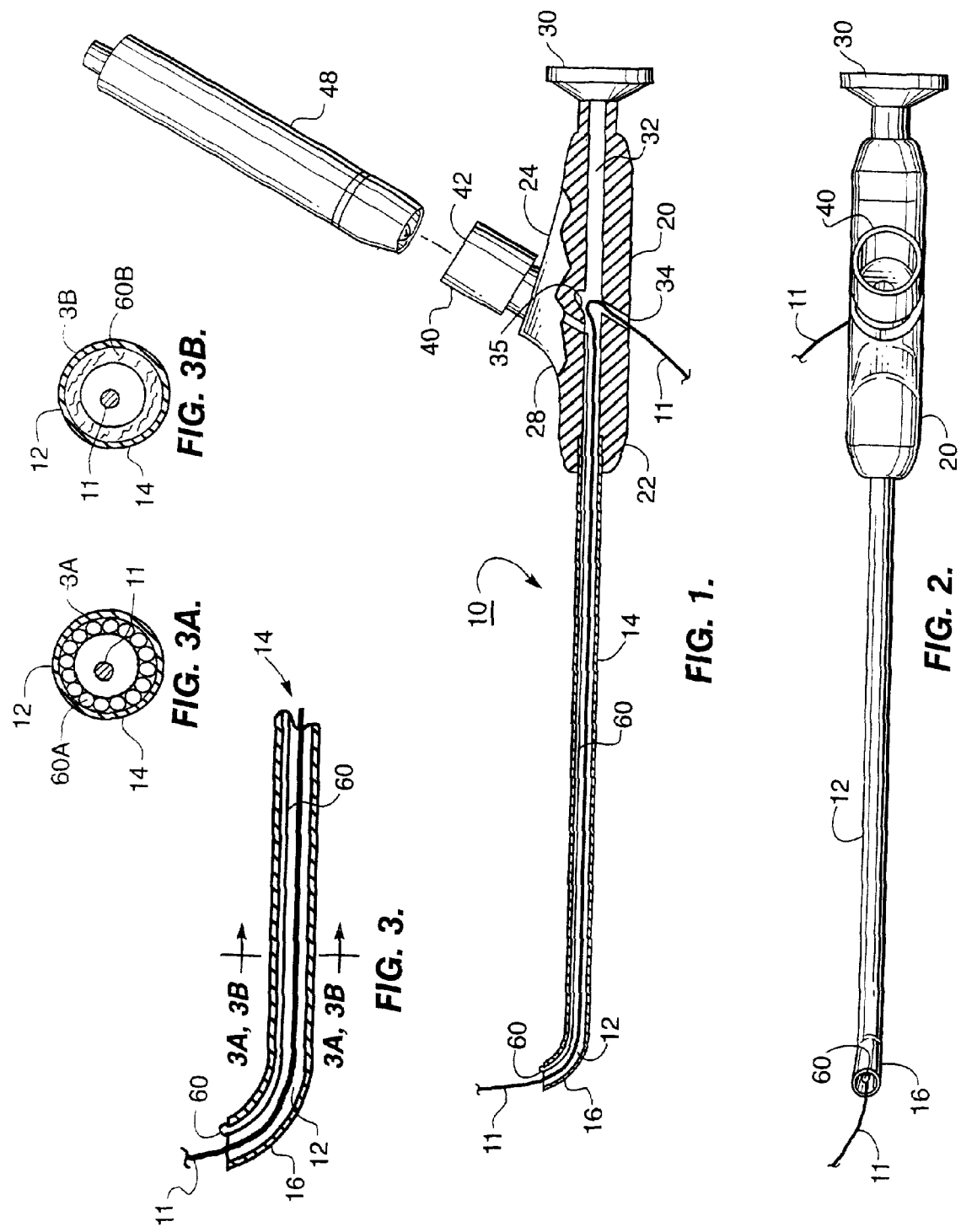

ENDOTRACHEAL TUBE GUIDE INTRODUCER AND METHOD OF INTUBATION

CROSS REFERENCE TO RELATED APPLICATION

The present application is a continuation-in-part of co-pending application Ser. No. 08/871,369, filed Jun. 9, 1997, entitled "Endotracheal Tube Guide Introducer", abandoned.

FIELD OF THE INVENTION

The present invention relates to a medical instrument used to facilitate insertion of an endotracheal tube into a patient's larynx and to a method of inserting an endotracheal tube into a patient's larynx. The instrument is of a type utilized by anaesthesiologists, paramedics and other emergency medical personnel.

BACKGROUND OF THE INVENTION

Endotracheal intubation is a medical procedure which involves the placement of a tube in the trachea of a patient to facilitate breathing or to permit controlled introduction of medical gases such as oxygen or anaesthesia through the tube.

Ordinarily endotracheal tubes are inserted into the patient's larynx by the use of a laryngoscope once the patient is sedated or anaesthetized. The laryngoscope consists of a handle generally held in the left hand of the attending physician having a blade which pushes the tongue and epiglottis out of the way to expose the vocal cords and the laryngeal opening.

In some instances, due to anatomical differences, the physician is unable to expose the opening. In such circumstances, the attending physician will have to resort to other means of insertion such as:

(1) Use of different kinds of blades including double angled blades, Jackson, Hollinger Jacks, Dido, Pilling and Tubular laryngoscopes. Other types of laryngoscopes may also be used such as Bellscope, bullards and others.

(2) Use of lighted wands may be required.

(3) In some instances, intubation may be by blind, oral or nasal procedures.

(4) Guides such as Bougies guides are also available.

(5) Surgical endoscopes which provide illumination means such as fiberoptic bronchoscopes may also be used.

(6) Retrograde intubation kits may also be used.

While these various other means and procedures are available, they have various disadvantages. For example, the blind insertion of a tube in the absence of visualization may lead to complications and may interfere with proper ventilation. Other types of devices require extreme dexterity and multi-handed operation on the part of the physician.

The prior patent literature also suggests various other intubation devices including the following:

U.S. Pat. No. 5,235,970 entitled "Tracheal Intubation With a Stylet Guide" shows a flexible stylet guide which has a curved tracheal seeking forward end shaped to follow the curvature of the back of the tongue and the anterior surface of the throat and a rear end projecting out of the mouth. The guide is inserted into the larynx blindly and requires use of an endotracheal tube and a tracheal intubation guide.

U.S. Pat. No. 5,016,614 entitled "Endotracheal Intubation Apparatus" consists of a handle and an elongated obturator element. An endotracheal tube is selectively ejected from the extended portion and visualization is provided by means of an endoscope. Also, the device may be provided with a suctioning element. The apparatus provides visualization and serves to inject an endotracheal tube directly into the larynx.

U.S. Pat. No. 5,352,237 shows an endoscope instrument including a handle having a flywheel mechanism which is used for retraction and better visualization of endoscopic procedures. A flexible member is secured about the flywheel spool and extends to a tool mechanism at the distal end of the instrument.

U.S. Pat. No. 5,058,577 discloses a flexible tip stylet for use with an endotracheal intubation device. The intubation tube stylet is within an intubation tube. The stylet tip is Z-shaped and is deformable to facilitate insertion into the larynx despite an obstruction. This endotracheal tube is then slipped along into the larynx.

U.S. Pat. No. 4,529,400 entitled "Apparatus For Naso and Oro Endotracheal Intubation" discloses a directable stylet for nasal or oral intubation. The stylet is directed by a hand-operated lever bar and grips support into an articulating wire with a curvature to facilitate intubation.

U.S. Pat. No. 4,329,983 entitled "Guide Device for Endotracheal Tube" includes a flexible bar inserted through an endotracheal tube. Flexible line extends along the bar. When the line is pulled, the length shortens and causes the inner portion of the bar to flex and causes the tip of the tube to be directed forward toward the trachea.

U.S. Pat. No. 4,949,716 entitled "Nasal Intubation Adjunct" shows a device with a stylet in a handle to control direction of the stylet within a nasal tracheal tube. No visualization is provided and the device requires use of a stethoscope to confirm proper placement.

U.S. Pat. No. 5,363,838 shows a fiber intubation scope with camera and light weight portable screen and a method of using the same. The fiber optic is inserted through an endotracheal tube to visualize the trachea through the camera and screen and the tube is inserted.

U.S. Pat. No. 5,507,279 shows a retrograde endotracheal intubation kit. The kit is used as a guide to introduce transtracheally and upward (cephalad) directed through the mouth wherein the guide is inserted through an endotracheal tube which is pushed down the trachea and the guide pulled out.

U.S. Pat. No. 5,498,231 discloses an intubating laryngoscope. This device consists of a handle with a battery and lighting device. The device has a hollow tube for an endotracheal tube. The hollow tube terminates at a pair of opposed blades perpendicular to the hollow body. The blades are provided with a hand-controlled lever to open and close the blades.

U.S. Pat. No. 5,323,771 shows an endotracheal tube introducer which consists of a curved tube inserted into the mouth and the tracheal tube is directed down into the trachea through an opening in the tube.

U.S. Pat. No. 5,394,865 shows a lighted stylet which is insertable into an endotracheal tube and is directed through the trachea by direct visualization through fiber optic scope.

U.S. Pat. No. 5,287,848 discloses a compact instrument which includes a handle with a curved lower blade. The instrument has pre-positioned endotracheal tube, fiberoptic visualization device and sectioned openings.

In spite of the various intubation devices available in the prior art, there nevertheless exists a need for an improved medical instrument for facilitating endotracheal intubation. Accordingly, it is an object of the present invention to provide an endotracheal tube guide introducer which is simple, easy to manufacture and relatively inexpensive.

It is a further object of the present invention to provide a medical instrument which is relatively easy for the practitioner to learn to use.

It is still another object of the present invention to provide a medical instrument which may be used in conjunction with a laryngoscope to facilitate better exposure.

It is yet another object of the present invention to provide a medical instrument which affords direct visualization and which may be detachable and sterilizable by conventional methods.

BRIEF SUMMARY OF THE INVENTION

The present invention provides an endotracheal tube guide introducer which is utilized in patients who, because of anatomical differences, make visualization of the larynx difficult or entirely obstructed and therefore are difficult to intubate by conventional means available.

The present invention may be used with the aid of a laryngoscope as ordinarily used to depress the tongue and the epiglottis out of the way. The instrument is inserted by direct visualization and manipulation until the vocal chords in the trachea are observed, much like direct bronchoscopy. The instrument is pushed down until the tip is close enough to the opening of the trachea and then the assistant pushes a guide tube down into the trachea. When approximately two to three inches of the guide tube is inserted, the attending medical personnel will slowly pull out the instrument leaving the guide stationary and pushing it down as the instrument is being removed. The proximal end of the guide is inserted into the distal end of an appropriate endotracheal tube until the guide is out the proximal end of the endotracheal tube. The endotracheal tube is then advanced into the trachea following the guide line. Once the endotracheal tube is in the trachea, the guide may be pulled out. The physician may check the position by auscultation of the chest.

The device consists of two coaxial tubes, one with optical means to transmit an image to the visualizing end and to transmit light to the distal end of the device. A rigid coaxial tube transmits a guide line through the proximal opening. The handle is configured for optimum maneuverability. The source of light may be a small flashlight or pen light which may be detachably connected to the handle.

In other embodiments, the device may be attached to the handle of a conventional laryngoscope. In another embodiment, the handle is a pistol grip type handle which houses a battery which powers the illumination source. In yet another embodiment, the device carries a mechanism for selectively advancing the guide tube in the form of one or more wheels or ratchets which rotate to advance the guide. The wheels may be manually or motor-operated.

BRIEF DESCRIPTION OF THE DRAWINGS

The above and other advantages of the present invention will be more fully understood from the following description, claims and drawings in which:

FIG. 1 is a side view of the endotracheal tube guide introducer of the present invention;

FIG. 2 is a top view of the introducer;

FIG. 3 is a detail view of the tip of the introducer;

FIGS. 3A and 3B are cross sections of the tip taken along lines 3—3 of FIG. 3 showing variations of the fiberoptic tube;

DETAILED DESCRIPTION OF THE DRAWINGS

Figure 4:
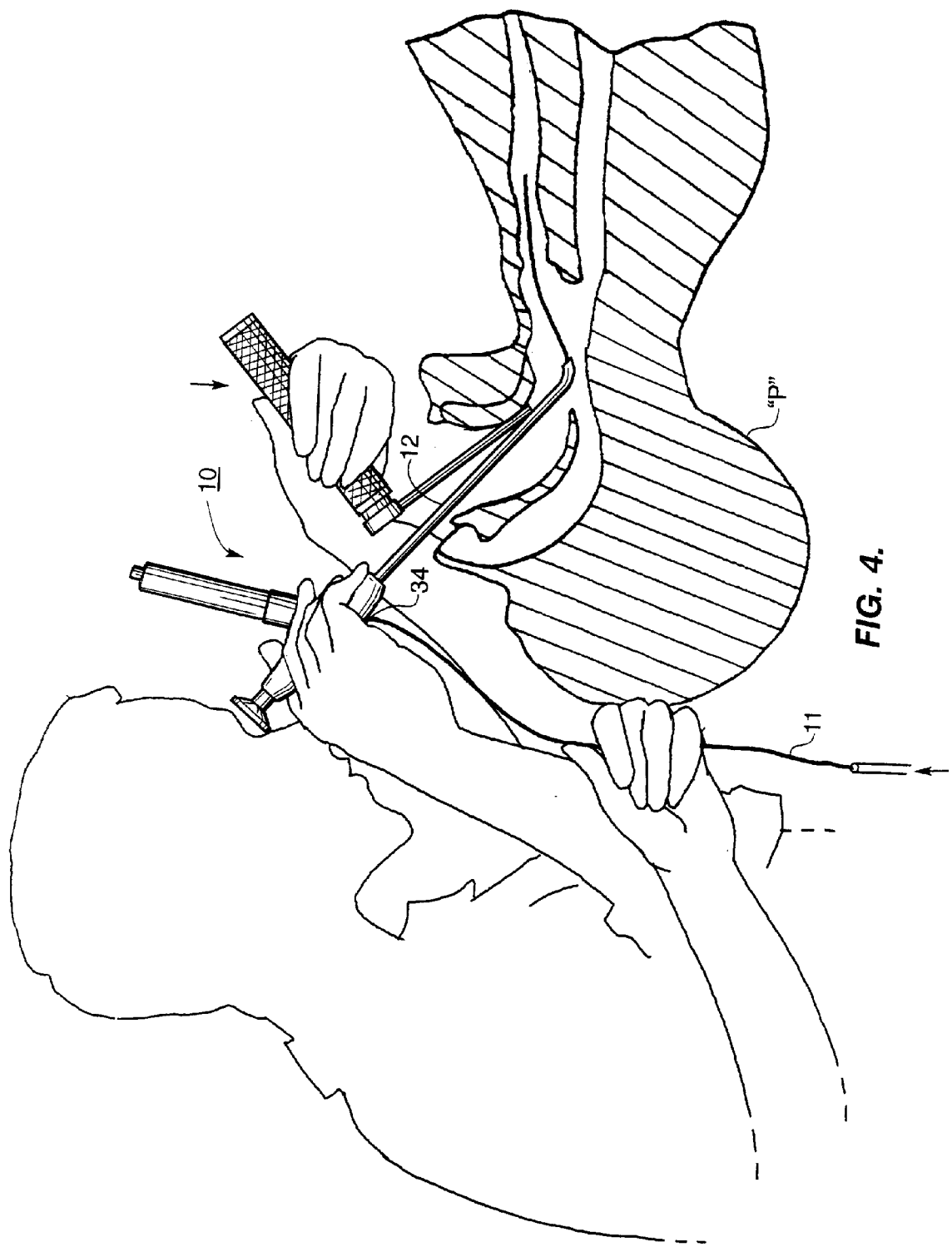
FIGS. 4 to 7 show the use of the device in connection with the laryngoscope illustrated in the manner in which the guide is inserted, pushed in place, positioned and followed by insertion of the endotracheal tube.

A preferred embodiment of the endotracheal tube guide introducer is illustrated in FIGS. 1 to 3. The tube guide introducer is generally designated by the numeral 10 and consists of an elongate, rigid tube 12 defining a lumen 14. The tube 12 is preferably of stainless steel or other sterilizable, rigid material. The distal end of the rigid tube 12 has a slightly upwardly curved tip 16. The opposite or proximal end of the tube 12 is received within a handle 20. The handle 20 is configured for comfort and ease of manipulization. Accordingly, the handle has a lower surface 22 which generally is parallel to the tube. In cross section, the handle is generally circular having an upper surface 24 which angles slightly upwardly. An arcuate or curved depression 28 extends in the forward end of the handle and extends generally downward toward the tube. The curved surface 28 is designed to receive the thumb of the user while the body portion of the handle is gripped with the fingers of the user.

The proximal end of the handle is provided with an eyepiece 30 for visualization. A longitudinally extending passageway 32 extends from the eyepiece 30 to the lumen of the tube. An angularly extending insertion passageway 34 is provided in the bottom of the handle and intersects the passageway 32 at the junction with the inner or proximal end of the lumen 14. A curved transition surface 35 is shown at the junction to assist in guiding and directing the guide tube properly into the lumen of the tube 12.

A port 40 also intersects the passageway 32 generally opposite the insertion passageway 34. The port 40 is provided with a coupling 42 which projects from the upper surface of the handle and is adapted to receive a light source such as a conventional pen light 48. The pen light 48 may be frictionally engaged within the coupling 42 and may be removed. As will be explained hereafter, a guide line 11 is inserted into the insertion passageway 34 where it is directed by the curved surface 35 into the lumen 14 of the rigid tube 12.

To assist in the procedure and to provide illumination and visualization, a fiberoptic tube 60 extends coaxially along the surface of guide tube 12. The fiberoptic tube 60 extends to a location within the handle at the intersection with the light port 40. As seen in FIG. 3A, the light transmitting fiberoptic tube may be an acrylic fiberoptic tube 60A or, as seen in FIG. 3B, a gel fiberoptic 60B as is conventionally used and well known to those in the art.

As set forth above, the endotracheal tube guide introducer 10 of the present invention is particularly beneficial when used with patients who are difficult to intubate. The introducer 10 provides a means of introducing a guide line into the larynx over which may be placed and inserted and directed through an endotracheal tube. The term guide line refers to any wire, cord, line of metal or other material along which a tube or instrument may be directed and guided.

Referring to FIGS. 4 to 7, which illustrate the use of the device, the patient "P" is unconscious or anaesthetized.

From a position above and forward of the patient's head, the conventional laryngoscope "L" is inserted in the usual manner with the patient's throat being initially sprayed with a topical antiseptic. The introducer 10 is advanced like a bronchoscope. It is to be noted that the shape of the handle provides the physician with good manipulative control. The physician is able, in most cases, to visualize the vocal cords although with some patients this is not possible.

With the right hand or by using an assistant, the physician places guide line 11 into the insertion passageway 34 in the handle of the device. The guide tube 11 is slowly advanced through the rigid tube 12. The introducer 10 is advanced beyond the uvula and epiglottis. The tip of the introducer is preferably inserted between the vocal cords. The assistant may then advance the guide tube until the tip extends down into the bronchus. At this position as shown in FIG. 4, the tip of the guide tube 11 is in proper position for insertion of the ET. The guide tube will now extend from the curved tip of the rigid tube into the bronchus.

Figure 5:
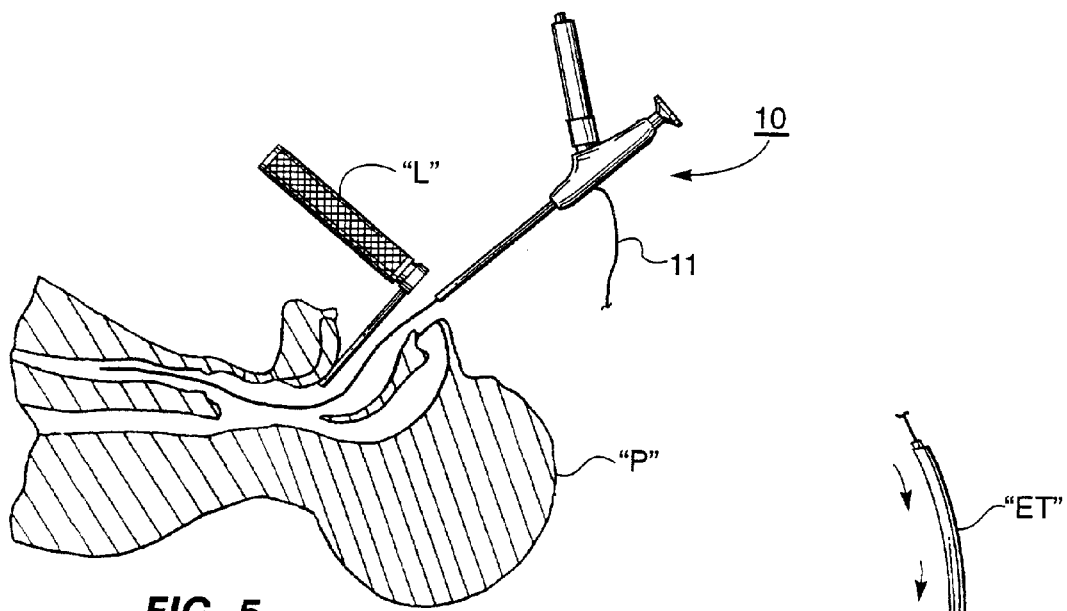

Referring to FIG. 5, the introducer may now be slowly removed leaving the guide line in place. As the introducer is withdrawn, the assistant will apply a slight pushing force on the proximal end of the guide line so that the guide line 11 remains in place as the introducer is withdrawn. In FIG. 5 the laryngoscope remains in position until the instrument is removed.

Figure 6:
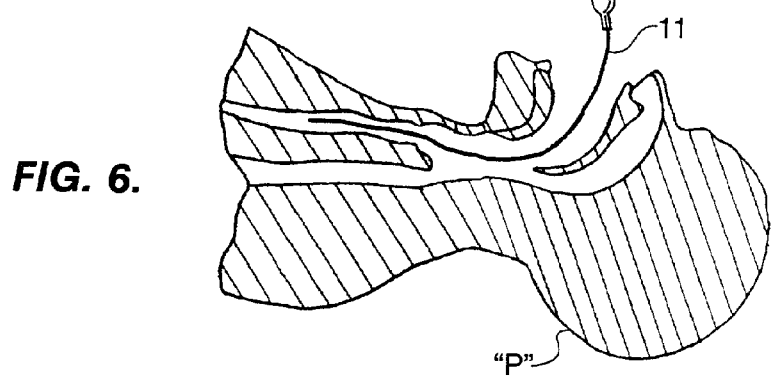
Figure 7:
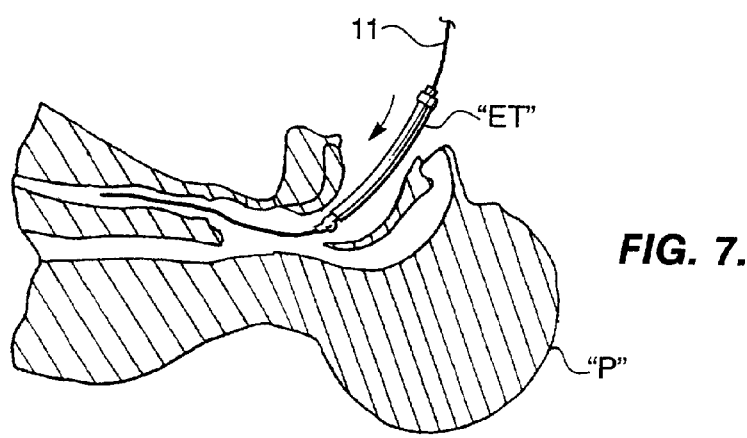

The proximal end of the guide line 11 may now be inserted into the distal end of the selected endotracheal tube "ET" along its entire length. The ET may be pushed down along the guide tube into the mouth and into the bronchus. The position is checked by auscultation and secured in place. FIG. 5 illustrates the introducer once it is removed, leaving the guide tube in place. FIG. 6 shows the guide line 11 being inserted into the distal end of endotracheal tube ET. FIG. 7 illustrates the endotracheal tube ET being advanced into the trachea along the guide tube until properly positioned.

Figure 8:
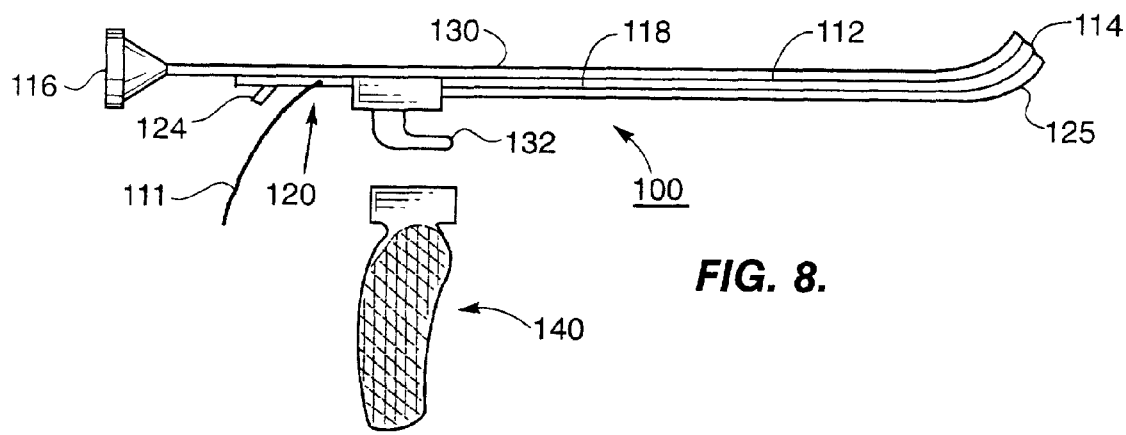
FIG. 8 is a side view of another embodiment of the present invention.

FIG. 8 illustrates an alternate embodiment of the introducer of the present invention which is generally designated by the numeral 100. In this embodiment, the introducer includes an elongate axially extending guide tube 112 which has an upwardly curved tip 114. The proximal end of the guide tube is provided with a viewer 116 which provides visualization through the lumen 118 of the guide tube. An aperture 120 is provided in the guide tube at an intermediate location which facilitates insertion of the guide line 111. Additional connections for oxygen or other gases may also be provided such as connection 124. A tube 125 for transmitting oxygen or other gases extends coaxially along the rigid guide tube. As has been described previously, a fiberoptic tube 130 may also be provided attached to the guide tube 112 for transmitting light and images from the distal end to the eye viewer 116.

A connector 132 is secured to the guide tube at an intermediate location spaced distally from the aperture 120. The connector 130 is a conventional connector to which a conventional laryngoscope handle 140 of conventional design may be attached. In this manner, the device is provided with a pistol grip type handle which may be preferred by some physicians. Further, some physicians may prefer to use the laryngoscope handle 140 because of familiarity.

The embodiment shown in FIG. 8 is used in the manner as described with reference to FIGS. 4 to 7 in which the introducer 100 is introduced beyond the uvula and epiglottis. Visualization of the vocal cords is provided through the eye viewer 116. Once the tip of the introducer is properly positioned between the vocal cords, the guide tube can be inserted into the aperture in the guide tube intermediate the eyepiece and the handle. The device can be properly manipulated by the physician using the handle and either the physician or the assistant can advance the guide cord until the tip extends into the bronchus.

Figure 9:
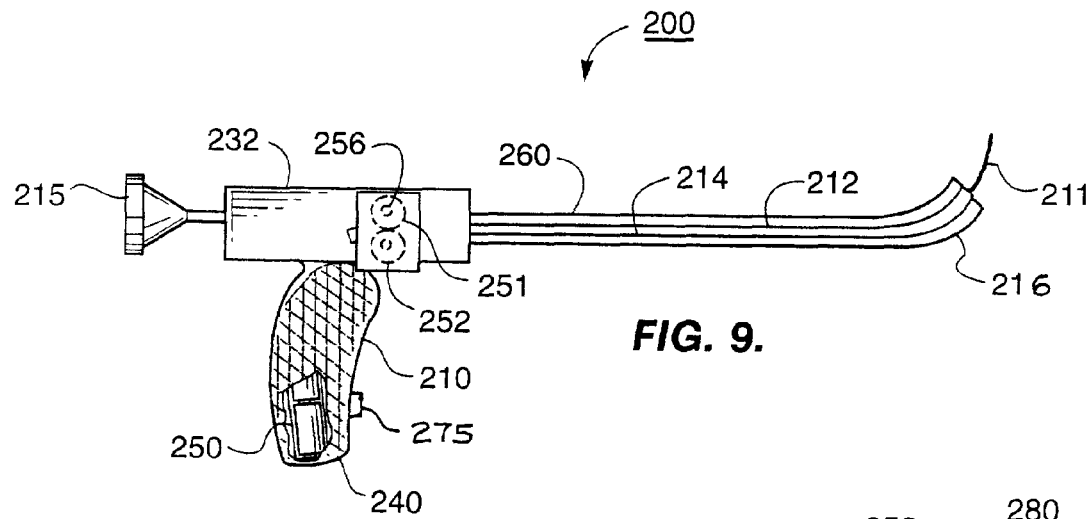
FIG. 9 is a side view of yet another embodiment of the present invention.
Figure 10:
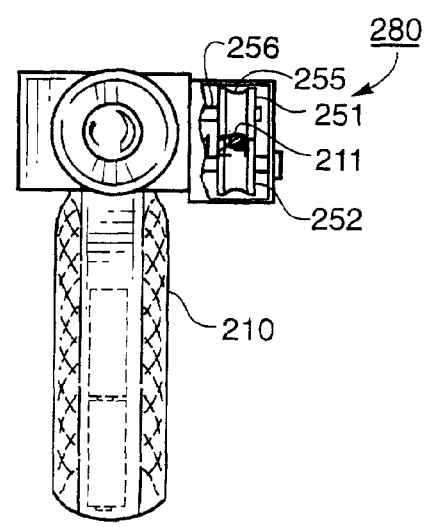
FIG. 10 is a rear view of the embodiment of the invention shown in FIG. 9.

FIGS. 9 and 10 show yet another embodiment of the introducer of the present invention generally designated by the numeral 200. Again, the introducer includes a longitudinally extending rigid guide tube 212 of stainless steel or other similar material having a lumen 214. The guide tube has a curved tip or distal end 216 and the tube extends through a handle 210 terminating at a viewer 215 at the proximal end. A fiberoptic light tube 260 is attached and extends coaxially along the rigid tube extending from the handle to the distal end 216. The handle is shown as a pistol grip type handle which has a body 232 which extends circumferentially around the rigid tube. A depending grip 240 which extends angularly with respect to the axis of the guide tube is provided. The grip is sized to be easily gripped in the fingers and palms of the hand of the user. An aperture extends in the rear of the body portion of the handle communicating with the lumen of the guide tube. The insertion aperture facilitates insertion of the guide wire or cord into the lumen of the guide tube.

A compartment 250 within the handle is adapted to receive and house an energy source such as one or more batteries which may be used to provide illumination which is transmitted along the fiberoptic tube so that the area at the end of the guide tube may be illuminated for better visualization.

In the embodiment of FIGS. 8 and 9, the advancement of the guide line is facilitated by a feed mechanism 280 which is positioned on the side of the handle. The feed mechanism consists of a pair of wheels 251 and 252, each of which are rotative about a shaft 256 attached to the handle. Preferably the surface of the wheel are either ribbed or provided with a slight concavity 255 as shown. The mating concavities are sized to approximate the diameter of the guide wire or cord. Accordingly, the guide line 211 is inserted between the wheels as best shown in FIG. 10. The device is used as described with reference to FIGS. 4 to 7 with the guide tube advanced either by manually turning the drive wheel or by energizing the motor at switch 275.

Accordingly, it will be seen that the present invention provides a tube guide introducer which is simple, relatively easy to master, and may be inexpensively manufactured. The device is versatile in that it may be used with a conventional handle such as a laryngoscope handle and may also be used to administer gases such as oxygen or used with a jet ventilator.

It will be obvious to those skilled in the art to make various changes, alterations and modifications to the tube guide introducer described herein. To the extent such changes, alterations and modifications do not depart from the spirit and scope of the appended claims, they are intended to be encompassed therein.

I claim:

1. A medical instrument for position a guide line in the trachea of the patient along which an ET may be inserted, said instrument comprising:
    (a) a rigid elongate tube having a distal and proximal end, said tube defining a lumen;
    (b) visualization means at the proximal end of said tube;
    (c) an introducer aperture communicating with said lumen for inserting a guide line in said lumen to extend to the proximal end;

(d) handle means associated with said rigid tube for manipulating the instrument and (e) said introducer aperture being generally transverse to said lumen and including a curved guide surface for directing a guide line into said lumen.

2. The medical instrument of claim 1 wherein said distal end is curved.

3. The medical instrument of claim 1 further including a fiberoptic tube extending along said rigid tube.

4. The medical instrument of claim 1 further including a second tube extending along said rigid tube for administering medical gases to the patient.

5. The medical instrument of claim 1 wherein said handle is generally configured in the form of a pistol grip.

6. The medical instrument of claim 1 wherein said handle is a conventional laryngoscope handle and said tube includes a connector for detachably securing said laryngoscope handle to said tube.

7. The medical instrument of claim 1 further including means for selectively advancing said guide line within said lumen.

8. The medical instrument of claim 7 wherein said means for selectively advancing said guide tube comprises a pair of rotatable wheels positioned adjacent one another on said handle and wherein said guide wire is insertable between said wheels.

9. The medical instrument of claim 8 wherein said wheels include means for manually rotating at least one of said wheels.

10. The medical instrument of claim 1 wherein said handle defines a battery receiving compartment.

11. The medical instrument of claim 10 wherein said battery is connected to motor means having drive means for selectively advancing and retracting said guide wire.

* * * * *